United States Patent [19]
De Munari et al.

[11] Patent Number: 5,914,324
[45] Date of Patent: Jun. 22, 1999

[54] 6-HYDROXY AND 6-OXO-ANDROSTANE DERIVATIVES ACTIVE ON THE CARDIOVASCULAR SYSTEM AND PHARMACEUTICAL COMPOSITIONS CONTAINING SAME

[75] Inventors: Sergio De Munari; Elena Folpini; Marco Frigerio; Piero Melloni, all of Milan; Fulvio Serra, San Ilario di Nerviano; Simona Sputore, Meda, all of Italy

[73] Assignee: Sigma-Tau Industrie Farmaceutiche Riunite S.p.A., Rome, Italy

[21] Appl. No.: 08/891,030

[22] Filed: Jul. 10, 1997

[30] Foreign Application Priority Data

Aug. 19, 1996 [DE] Germany ............... 196 33 349

[51] Int. Cl.[6] ............... A61K 31/56; C07J 1/00
[52] U.S. Cl. ............... 514/178; 514/177; 514/182; 514/255; 514/315; 514/396; 544/224; 544/388; 546/195; 548/335.5; 548/336; 548/529; 552/641; 552/622; 552/633
[58] Field of Search ............... 552/641, 633, 552/622; 514/182, 178, 177, 428, 396, 315, 255; 548/335.5, 336.3, 529; 546/195; 544/224, 388

[56] References Cited

U.S. PATENT DOCUMENTS

| 2,863,885 | 12/1958 | Babcock ............... 260/397 |
| 3,646,064 | 2/1972 | Anner et al. ............... 260/340.9 |
| 5,444,055 | 8/1995 | Cerri et al. ............... 514/182 |
| 5,583,127 | 12/1996 | Cerri et al. ............... 514/175 |

FOREIGN PATENT DOCUMENTS

WO 93/14105  7/1993  WIPO .

OTHER PUBLICATIONS

Sergio Bova, et al., Hypertension, vol. 17, No. 6, pp. 944–950, "Effects of an Endogenous Quabainlike Compound on Heart and Aorta", Jun. 1991.

Fabio Celotti, et al., J. Steroid Biochem., vol. 18, No. 4, pp. 397–401, "Effects of 6– and 7–Hydroxy Metabolites of 3β, 17β–Dihydroxy–5α–Androstane on Gonadotrophin and Prolactin Secretion and on Sex Accessories Weight of Male Rats", 1983.

H. J. G. M. Derks, et al., Steroids, vol. 31, No. 2, pp. 289–290 and 302–304, "The Indentification and Quanitification of Three New 6α–Hydroxylated Corticosteroids in Human Neonatal Urine", Feb. 1978.

Peter H. Jellinck, et al., J. Steroid Biochem. Molec. Biol., vol. 39 , No. 6, pp. 947–951, "Suppression of 5α–Androstane–3β, 17β–Diol Hydroxylase Activity in Rat Pituitary by Cobalt Protoporhyrin: Implications for Testosterone Homeostasis", 1991.

Susumu Miyabo, et al., Folia Endocrinol. Jap., vol. 52, pp. 630–636, "Cortisol Metabolites in Human and Dog Plasma a Comparative Study", 1976, (with partial English translation).

John Orlowski, et al., Endocrinology, vol. 128, No. 2, pp. 872–884, "Epithelial–Stromal Interactions in The Regulation of Rat Ventral Prostate Function: Indentification and Characterization of Pathways for Androgen Metabolism in Isolated Cell Types", 1991.

Kenneth D. R. Setchell, FEBS Letters, vol. 70 , No. 1, pp. 197–200, "6–Hydroxylation, an Important Route in the Metabolism of Corticosteroids by the Baboon: The Fate of Administered Tetrahydrocortisol", Nov. 1976.

John. F. Templeton, et al., J. Chem. Soc. Perkin Trans., vol. 1, pp. 1361–1368, "Synthesis of Ring–A and –B Substituted 17α–Acetoxypregnan–20–One Derivatives with Potential Activity on the Digital Receptor in Cardiac Muscle", 1987.

John. F. Templeton, et al., Steroids, vol. 49, pp. 383–396, "Structure–Activity Relationships of Progesterone Derivatives that bind to the Digitals Receptor: Modifications in A and B Rings", Apr.–May 1987.

Chemical Abstracts, vol. 114, p. 89, AN–136215d, 1991.

Chemical Abstracts, vol. 109, p. 68, AN–17146u, 1988.

Chemical Abstracts, vol. 119, p. 1037, AN–271486m, 1993.

Chemical Abstracts, vol. 116, p. 87, AN–99567p, 1992.

*Primary Examiner*—Dwayne C. Jones
*Attorney, Agent, or Firm*—Oblon, Spivak, McClelland, Maier & Neustadt, P.C.

[57] ABSTRACT

6-hydroxy and 6-oxo-androstane derivatives of formula (I), active on the cardiovascular system.

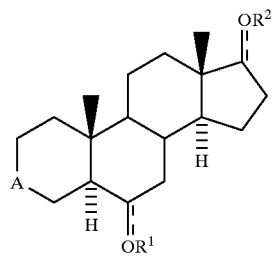

wherein:

the symbol A represents CH—OR, C=N—OR, CH—CH=N—OR and C=CH—N—OR; and $R^1$, $R^2$ and $R^3$ are as defined herein.

8 Claims, No Drawings

6-HYDROXY AND 6-OXO-ANDROSTANE DERIVATIVES ACTIVE ON THE CARDIOVASCULAR SYSTEM AND PHARMACEUTICAL COMPOSITIONS CONTAINING SAME

BACKGROUND OF THE INVENTION

1. Field of the Invention

The present invention relates to new 6-hydroxy and 6-oxo-androstane derivatives and to pharmaceutical compositions containing same for the treatment of cardiovascular disorders such as heart failure and hypertension.

2. Summary of the Invention

The compounds of the invention have the following general formula (I):

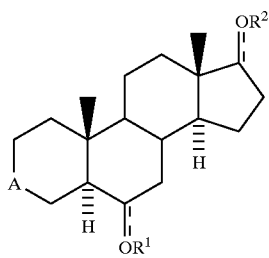

wherein:
the symbol A represents CH—OR, C=N—OR, CH—CH=N—OR and C=CH—CH=N—OR,
where:
R represents a C2–C6 alkyl group substituted by $NR^3R^4$, $NHC(NH)NHR^5$, $C(NH)NR^6R^7$ or —O—(C2–C4-alkyl)-$NR^3R^4$ groups,
wherein $R^3$ and $R^4$, which may be the same or different, are H. C1–C6 lower alkyl group, benzyl or phenyl or $R^3$ and $R^4$, taken together with the nitrogen atom, form an unsubstituted or substituted saturated or unsaturated mono-heterocyclic 5- or 6-membered ring optionally containing another heteroatom chosen from oxygen, sulphur or nitrogen,
$R^5$, $R^6$ and $R^7$, which are the same or different, may be H or C1–C4 lower alkyl;
the symbol ———. in position 6 and in position 17 represents independently a single or a double bond;
when the symbol ———. represents a single bond
$R^1$ represents H, C1–C4 lower alkyl and C2–C6 acyl groups;
$R^2$ represents H, methyl, C2–C6 alkyl group unsubstituted or substituted by $NR^3R^4$, C2–C6 acyl groups, benzoyl, benzoyl substituted by one or more hydroxy, methoxy, amino, chloro, fluoro, methylmercapto groups.
when the symbol ———. represent a double bond, it means a keto group and no $R^1$ or $R^2$ is present.

The invention includes within its scope all the possible stereoisomers, in particular Z and E isomers and syn and anti isomers, optical isomers and their mixtures of the compounds of formula (I).

Also included in this invention are pharmaceutically acceptable salts of (I), which retain the biological activity of the base and are derived from known acids such as, for example, hydrochloric, sulphuric, phosphoric, malic, tartaric, maleic, citric, methanesulfonic, benzoic acid or other acids used in the art.

DETAILED DESCRIPTION OF THE INVENTION

The alkyl and alkenyl groups may be branched or straight chain groups. The C2–C6 alkyl group is preferably a C2–C4 alkyl group, e.g. ethyl, n-propyl, iso-propyl, n-butyl, sec-butyl. The C2–C6 acyl is preferably a C2–C4 acyl group, e.g. acetyl, propionyl, butyryl. The $NR^3R^4$ group is preferably amino, methylamino, ethylamino, n-propylamino, iso-propylamino, allylamino, propargylamino, N,N-dimethylamino, N,N-diethylamino, N,N-di-n-propylamino, N,N-di-iso-propylamino, pyrrolidinyl, piperidino, morpholino, 4-methyl-piperazin-1-yl, 1-imidazolyl. The —O—C2–C4-alkyl-$NNR^3R^4$ group is preferably 2-amino-ethoxy, 2-N,N-dimethylamino-ethoxy, 2-(1-pyrrolidinyl) ethoxy.

Preferred examples of specific compounds (I) according to the present invention are:
3β-(4-N-ethylaminobutoxy)-5α-androstan-6,17-dione
3β-(2-N,N-dimethylaminoethoxy)-5α-androstan-6,17-dione
3α-(3-N,N-dimethylaminopropoxy)-5α-androstan-6,17-dione
3β-(3-N,N-dimethylaminopropoxy)-5α-androstan-6,17-dione
3β-(4-N,N-dimethylaminobutoxy)-5α-androstan-6,17-dione
3β-(2-N-pyrrolidinylethoxy)-5α-androstan-6,17-dione
3β-[2-(2-N,N-dimethylaminoethoxy)ethoxy]-5α-androstan-6,17-dione
3β-[2-(2-N-pyrrolidinylethoxy)ethoxy]-5α-androstan-6,17-dione
3β-(2-N-imidazolylethoxy)-5α-androstan-6,17-dione
3β-(3-N-imidazolylpropoxy)-5α-androstan-6,17-dione
3β-(2-N-piperidinoethoxy)-5α-androstan-6,17-dione
3β-[2-(4-methylpiperazin-1-yl)ethoxy)]-5α-androstan-6,17-dione
3β-(2-aminoethoxy)-5α-androstan-6α,17β-diol
3β-(3-aminopropoxy)-5α-androstan-6α,17β-diol
3β-(3-N-methylaminopropoxy)-5α-androstan-6α,17β-diol
3β-(2-N,N-dimethylaminoethoxy)-5α-androstan-6α,17β-diol
3α-(3-N,N-dimethylaminopropoxy)-5α-androstan-6α,17β-diol
3β-(3-N,N-dimethylaminopropoxy)-5α-androstan-6α,17β-diol
3β-(4-N,N-dimethylaminobutoxy)-5α-androstan-6α,17β-diol
3β-(2-N-pyrrolidinylethoxy)-5α-androstan-6α,17β-diol
3β-[2-(2-N,N-dimethylaminoethoxy)ethoxy]-5α-androstan-6α,17β-diol
3β-[2-(2-N-pyrrolidinylethoxy)ethoxy]-5α-androstan-6α,17β-diol
3β-(2-aminoethoxy)-5α-androstan-6β,17β-diol
3β-(3-N,N-dimethylaminopropoxy)-5α-androstan-6β,17β-diol
3β-(2-guanidinoethoxy)-5α-androstan-6α,17β-diol
3β-(3-guanidinopropoxy)-5α-androstan-6β,17β-diol
3β-(2-guanidinoethoxy)-5α-androstan-6β,17β-diol
3β-[2-(2-N,N-dimethylaminoethoxy)ethoxy]-5α-androstan-6β,17β-diol 3β-(2-N,N-dimethylaminoethoxy)-5α-androstan-17β-acetate-6α-ol 3β-(3-N,N-dimethylaminopropoxy)-5α-androstan-17β-acetate-6α-ol 3β-(3-N,N-dimethylaminopropoxy)-5α-androstan-17β-benzoate-6α-ol 3β-(3-N,N-dimethylaminopropoxy)-5α-androstan-17β-(2-N,N-dimethylaminoethoxy)-6α-ol 3β-(2-aminoethoxy)-5α-androstan-6α-hydroxy-17-one 3β-(2-N-nethylaminoethoxy)-5α-androstan-6α-hydroxy-17-one 3β-(3-N,N-dimethylaminopropoxy)-5α-androstan-6α-hydroxy-17-one 3β-(2-N,N-dimethylaminoethoxy)-5α-androstan-17β-hydroxy-6-one (E,Z)-3-(2-aminoethoxyimino)-5α-androstan-6,17-dione (E)-3-(2-aminoethoxyimino)-5α-androstan-6,17-dione (Z)-3-(2-aminoethoxyimino)-5α-androstan-6,17-dione (E)-3-(2-N,N-dimethylaminoethoxyimino)-5α-androstan-6,17-dione (Z)-3-(2-N,N-dimethylaminoethoxyimino)-5α-androstan-6,17-dione (E)-3β-(2-aminoethoxyiminomethyl)-5α-androstan-6,17-dione (Z)-3β-(2-aminoethoxyiminomethyl)-5α-androstan-6,17-dione (E)-3β-(2-N,N-dimethylaminoethoxyiminomethyl)-5α-androstan-6,17-dione (Z)-3β-(2-N,N-dimethylaminoethoxyiminomethyl)-5α-androstan-6,17-dione (E)-3-[3-(2-N,N-dimethylaminoethoxyimino)(E)-propen-1-yl)-5α-androstan-6,17-dione (Z)-3-[3-(2-N,N-dimethylaminoethoxyimino)(E)-propen-1-yl)-5α-androstan-6,17-dione (E)-3-[3-(2-N,N-dimethylaminoethoxyimino)(Z)-propen-1-yl)-5α-androstan-6,17-dione (Z)-3-[3-(2-N,N-dimethylaminoethoxyimino)(Z)-propen-1-yl)-5α-androstan-6,17-dione (E,Z)-3-(2-aminoethoxyimino)-5α-androstan-6α,17β-diol (E)-3-(2-N,N-dimethylaminoethoxyimino)-5α-androstan-6α,17β-diol (Z)-3-(2-N,N-dimethylaminoethoxyimino)-5α-androstan-6α,17β-diol (E)-3β-(2-aminoethoxyiminomethyl)-5α-androstan-6α,17β-diol (Z)-3β-(2-aminoethoxyiminomethyl)-5α-androstan-6α,17β-diol (E)-3β-(2-N,N-dimethylaminoethoxyiminomethyl)-5α-androstan-6α,17β-diol (Z)-3β-(2-N,N-dimethylaminoethoxyiminomethyl)-5α-androstan-6α,17β-diol (E)-3-[3-(2-N,N-dimethylaminoethoxyimino)(E)-propen-1-yl)-5α-androstan-6α,17β-diol (Z)-3-[3-(2-N,N-dimethylaminoethoxyimino)(E)-propen-1-yl)-5α-androstan-6α,17β-diol (E,Z)-3-[3-(2-N,N-dimethylaminoethoxyimino)(Z)-propen-1-yl)-5α-androstan-6α,17β-diol (E)-3-[3-(2-N,N-dimethylaminoethoxyimino)(Z)-propen-1-yl)-5α-androstan-6α,17β-diol (Z)-3-[3-(2-N,N-dimethylaminoethoxyimino)(Z)-propen-1-yl)-5α-androstan-6α,17β-diol 6-Hydroxy steroids are steroid metabolites produced both in humans and in animals such as rat, dog or baboon (Derks H. J. G. M. and Drayer N. M., Steroids 1978, 289; Setchell K. D., FEBS Lett. 1976, 70, 197; Miyabo S., Kishida S., Asato T. and Saito Z., Nippon Naibumpi Gakkai Zasshi 1976, 52, 630; Jellink H. P. and Galraith A. R., J. Steroid Biochem. Mol. Biol. 1991, 39, 947). The main function of 6-hydroxylation process is supposed to be the elimination of the parent steroid (Jellink H. P. loc.cit., Orlowski J. and Clark A. F., Endocrinology 1991, 128, 872). Simple 6-hydroxy and 6-oxo-androstane, such as for example 5α-androstane-3β,6α,17β-triol or 3β,17β-diacetoxy-5α-androstan-6-one are known compounds (Isaacs J. T., McDermott I. R. and Coffey D. S., Steroids 1979, 33, 639). Also known compounds are pregnane derivatives such as 17α-acetate-3α,6α-dihydroxy-5α-pregnan-20-one or 3β,17α-diacetate-5α-pregnan-6,20-dione (Templeton J. F. and Kumar V. P. S., J.Chem.Soc., Perkin Trans. I 1987, 1361). Said derivatives are described as devoid of pharmacological activity (Isaacs J. T. loc. cit.; Templeton J. F. loc. cit.; Templeton J. F., Kumar V. P. S., Kim S. R. and LaBella F. S., Steroids 1987, 383; Celotti F., Avogadri N., Ferraboschi P., Motta M., Negri-Cesi P. and Santaniello E., J. Steroid Biochem. 1983, 397) and indeed they are usually prepared as intermediate for the synthesis of derivatives in which the group linked to position 6 is different from oxygen (e.g.: methyl, methylene, fluorine, chlorine, bromine. See for example: Templeton J. F. loc. cit.; Buzzetti F., Longo A., Crugnola A., Di Salle E., WO 93 14,105). Structural as well as pharmacobiological differences between the compounds (I) of the present invention and the already known 6-oxo and 6-hydroxyandrostanes are evident.

The invention furthermore provides a process for the preparation of compounds of general formula (I) which comprises the condensation of compounds of general formula (II):

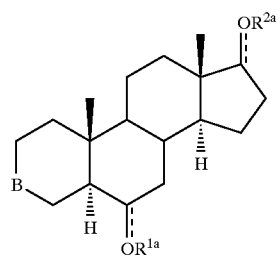

II where the symbol B represents CH—OH, C=O, CH—CH=O or CH=CH—CH=O, the symbol ———— represents a single o double bond and $R^{1a}$ has the same meanings of $R^1$ or it represents a hydroxy protecting group such as a silyl group, $R^{2a}$ has the same meanings of $R^2$ or it represents a hydroxy protecting group such as a silyl group, with a compound of general formula (III) when B represents CH—OH,

R—X            III where R is as already defined, and where X is a good leaving group such as halogen, mesyloxy, tosyloxy or trifluoroacetoxy group and with a compound of general formula (IV) when B represents C=O, CH—CH=O or CH=CH—CH=O

R—ONH$_2$            IV where R is as already defined with, if desired, the free hydroxy and/or the amino groups optionally present in R, $R^{1a}$ and/or $R^{2a}$ are protected with methods well known by those skilled in the art, to give, if necessary after removal of known protective groups possibly present in R, $R^{1a}$ and/or $R^{2a}$, a compound of general formula (I) which may be converted into another compound of general formula (I) and/or, if desired, subjected to salification and/or isomer separation. The reaction between a compound of general formula (II) and a compound of general formula (III) is best carried out in an inert solvent, such as tetrahydrofuran, dioxane, dimethylformamide, dimethylsulfoxyde, benzene, toluene, dichloromethane, chloroform or their mixtures in the presence of a condensing agent such as a strong base (e.g.: sodium or potassium hydride), or an acid (e.g.: p-toluensulfonic acid, hydrogen chloride, trifluoroacetic acid) or a heavy metal salt (e.g.: silver carbonate, silver oxide, silver triflate, mercury oxide or mercury tetrafluoborate) at a temperature ranging from −10° C. to the reflux temperature of the reaction mixture. The reaction between a compound of general formula (II) and a compound of general formula (IV) is best carried out in a solvent such as tetrahydrofuran, dioxane, dimethylformamide, dimethylsulfoxide, benzene, toluene, dichloromethane, methanol, ethanol, water or their mixtures, at a temperature ranging from 0° C. to the reflux temperature of the reaction mixtures. The reaction may be performed in the presence of a base, such as sodium or potassium hydroxide, sodium or potassium carbonate, or in presence of an acid such as, hydrochloric acid, hydrobromic acid or acetic acid. The reaction time varies from a few minutes to several hours.

All said transformations are only examples of well established procedures described in Organic Chemistry (see for example: J. March "Advanced Organic Chemistry", J. Wiley & Sons, 1992; D. Barton and W. D. Ollis "Comprehensive Organic Chemistry", Pergamon Press, 1979) well known to those skilled in the art.

The compounds of general formula (II) are prepared from prasterone (V):

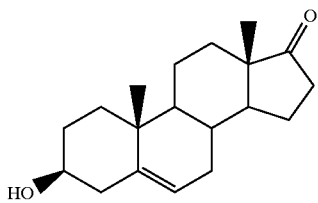

V by a series of known chemical transformation that comprise for example the oxidation of hydroxy group into a keto group, the oxidation of a double bond to alcohol, the transformation of a keto group into the homologous aldehyde, the transformation of a keto group into the vinilogous ester and reduction of an ester to the corresponding aldehyde or alcohol, as well as protection and deprotection of hydroxy and keto groups, by standard methods well known by those skilled in the art.

Compounds of general formula (III) and (IV) are known compounds, often commercially available or preparable from commercially available compounds by standard procedures. Prasterone (V) is commercially available.

We have found that the derivatives (I), prepared according to the invention, and their pharmaceutically acceptable salts are useful agents for the treatment of cardiovascular disorders, such as heart failure and hypertension. Moreover said compounds show affinity and inhibit the enzymatic activity of the $Na^+,K^+$-ATPase. To test the affinity for the receptor site of the $Na^+,K^+$-ATPase and the inhibitory activity on the enzyme, the following tests were used: a) displacement of the specific 3H-ouabain binding from the $Na^+,K^+$-ATPase receptor purified according to Jorghensen (Jorghensen P., BBA. 1974, 356, 36) and Erdmann (Erdmann E. et al., Arzneim.Forsh., 1984, 34, 1314); b) inhibition of the activity of the purified $Na^+,K^+$-ATPase measured as % of hydrolysis of 32P-ATP in presence and in absence of the tested compound (Mall F. et al., Biochem.Pharmacol., 1984, 33, 47). Moreover the compounds of the invention possesses positive inotropic features, as shown in electrically paced guinea pig left atrium according to Bova (Bova S., Blaustein M. P., Ludens J. H., Harries D. W., Ducharme D. W. and Hamlyn J. M. Hypertension 1991, 17, 944).

Finally the compounds of the invention have a low toxicity when compared with standard cardiotonic steroids. The activity of some compounds of general formula (I) on the above mentioned tests are shown in the following Table 1.

TABLE 1

| Example n° | Binding to Na,K-ATPase $EC_{50}$ ($\mu M$) | Inhibition of Na,K-ATPase $IC_{50}$ ($\mu M$) | Inotropic activity in vitro $EC_{50}$ ($\mu M$) | Acute toxicity mouse oral $LD_{50}$ (mg/kg) |
|---|---|---|---|---|
| Digoxin | 0.06 | 0.5 | 0.5 | 18 |
| I-a | 0.10 | 1.6 | 2.5 | >600 |
| I-d | 0.13 | 1.6 | 10.5 | >600 |
| I-e | 0.16 | 2.0 | 5.6 | >600 |
| I-f | 0.10 | 1.0 | 0.8 | 560 |
| I-h | 0.02 | 0.3 | 0.6 | 520 |
| I-i | 0.50 | 12.0 | 7.1 | >1000 |
| I-k | 0.32 | 3.2 | 12.6 | >600 |
| I-m | 1.30 | 50.0 | 20.0 | >1000 |

To obtain the desired therapeutic effect, the compound of the invention of general formula (I) may be administered, by oral, parenteral, nasal or rectal route, to the patient in pharmaceutical preparations. A pharmaceutical composition suitable for this purpose can be prepared according to well known techniques.

The following examples illustrate the invention without limiting it.

EXAMPLE 1

(E,Z)-3-(2-aminoethoxyimino)-5α-androstan-6α,17β-diol oxalate (I-a)

A solution of O-(2-aminoethyl)-hydroxylamine dihydrochloride (350 mg) in water (4 mL) was added to a solution of 3-oxo-5α-androstan-6α,17β-diol (II-b, Prep. 2, 500 mg) in dioxane (4 mL) and the resulting mixture was stirred for 2 hrs. Sodium hydroxide (1N) was added to pH=9 and the mixture was extracted with chloroform (5×20 ml). The combined organic layers were dried over sodium sulfate and evaporated to dryness under reduced pressure. The residue was purified by flash chromatography ($SiO_2$, chloroform/methanol/ammonia 90/10/1) to give 460 mg of (E,Z)-3-(2-aminoethoxyimino)-5α-androstan-6α,17β-diol, that were dissolved in ethyl acetate/methanol 70/30 (5 mL) and treated with oxalic acid (110 mg) to give 510 mg of (E,Z)-3-(2-aminoethoxyimino)-5α-androstan-6α,17β-diol oxalate (I-a), as a white podwer mp 151–156° C.

EXAMPLE 2
(E)-3-(2-N,N-dimethylaminoethoxyimino)-5α-androstan-6α,17β-diol (I-b)
(Z)-3-(2-N,N-dimethylaminoethoxyimino)-5α-androstan-6α,17β-diol (I-c)

A solution O-(2-N,N-dimethylaminoethyl)-hydroxylamine dihydrochloride (425 mg) in water (5 mL) was added to a solution of 3-oxo-5α-androstan-6α,17β-diol (II-b, Prep. 2, 500 mg) in dioxane (15 mL). Hydrochloric acid (1N) was added to pH=1 and the resulting mixture was stirred overnight. Sodium hydroxide (4N) was added to pH=10.5 and the mixture extracted with ethyl acetate (3×50 mL). The combined organic layers were dried over sodium sulfate and evaporated to dryness under reduced pressure. The residue (640 mg) was purified by flash chromatography (SiO$_2$, chloroform/methanol/ammonia 90/10/1) to give 240 mg of a fraction A and 180 mg of a fraction B. Fraction A crystallized from ethyl acetate/methanol 70/30 to give 46 mg of (Z)-3-(2-N,N-dimethylaminoethoxyimino)-5α-androstan-6α,17β-diol (I-c), as a white podwer mp 117–120° C. Fraction B crystallized from ethyl acetate/diethyl ether 50/50 to give 33 mg, of (E)-3-(2-N,N-dimethylaminoethoxyimino)-5α-androstan-6α,17β-diol (I-b), as a white podwer mp 102–106° C.

EXAMPLE 3
(Z)-3β-(2-aminoethoxyiminomethyl)-5α-androstan-6α,17β-diol oxalate (I-d)

A solution of 3-formyl-5α-androstan-6α,17β-diol (II-c, Prep. 3, 240 mg) in dioxane/water (2/1, 30 mL) was treated with sodium hydroxide (0.1 N) to pH=13–14 and stirred for 15 minutes, then a solution O-(2-aminoethyl)-hydroxylamine dihydrochloride (170 mg) in water (3 mL) was poured in. After 1 hr. the organic solvent was distilled off and the acqueous solution was extracted with chloroform (5×20 mL). The combined organic layers were dried over sodium sulfate and evaporated to dryness under reduced pressure. The residue was purified by flash chromatography (SiO$_2$, chloroform/methanol/ammonia 90/10/1) to give (Z)-3β-(2-aminoethoxyiminomethyl)-5α-androstan-6α,17β-diol, which was dissolved in ethyl acetate/methanol 70/30 and treated with oxalic acid to give 85 mg of (Z)-3β-(2-aminoethoxyiminomethyl)-5α-androstan-6α,17β-diol oxalate (I-d) as a white solid mp 190–192° C.

EXAMPLE 4
(Z)-3β-(2-N,N-dimethylaminoethoxyiminomethyl)-5α-androstan-6α,17β-diol oxalate (I-e)

Using the same reaction conditions described in Ex. 3, and starting from 3-formyl-5α-androstan-6α,17β-diol (II-c, Prep. 3) and O-(2-N,N-dimethylaminoethyl)-hydroxylamine dihydrochloride the title compound (Z)-3β-(2-N,N-dimethylaminoethoxyiminomethyl)-5α-androstan-6α,17β-diol oxalate (I-e), mp 113–114° C., was obtained in 42% yield.

EXAMPLE 5
(E)-3-[3-(2-N,N-dimethylaminoethoxyimino)(E)-propen-1-yl]-5α-androstan-6α,17β-diol (I-f)

A solution of O-(2-N,N-dimethylaminoethyl)-hydroxylamine dihydrochloride (215 mg) in "pH 7 buffer solution" (Janssen 25.859.57, 5 mL) was slowly dropped into a solution of (E)-3-formylmethylen-5α-androstan-6α,17β-diol (II-d, Prep. 4, 240 mg) in dioxane (20 mL) and "pH 7 buffer solution" (5 mL). During the addidition of the reactant, the pH of the reaction mixture was kept between 4 and 6.5 by addition of sodium hydroxide (0.1 N). After 2 hrs, sodium hydroxide (4N) was added to pH=7.5 and the mixture extracted with chloroform (3×50 mL). The combined organic layers were dried over sodium sulfate and evaporated to dryness under reduced pressure. The residue (304 mg) was purified by flash chromatography (SiO$_2$, chloroform/methanol/ammonia 95/5/0.1) to give, after trituration with diisopropyl ether, 100 mg of (E)-3-[3-(2-N,N-dimethylaminoethoxyimino)(E)-propen-1-yl]-5α-androstan-6α,17β-diol (I-f) as a pale white solid mp 110–115° C.

EXAMPLE 6
(E,Z)-3-[3-(2-N,N-dimethylaminoethoxyimino)(Z)-propen-1-yl]-5α-androstan-6α,17β-diol (I-g)

A solution of O-(2-N,N-dimethylaminoethyl)-hydroxylamine dihydrochloride (215 mg) in "pH 10 buffer solution" (Janssen 25.860.58, 10 mL) was slowly dropped into a solution of (Z)-3-formylmethylen-5α-androstan-6α,17β-diol (II-e, Prep. 4, 240 mg) in dioxane (12 mL) and "pH 10 buffer solution" (5 mL). After 36 hrs the mixture was extracted with chloroform (3×70 mL). The combined organic layers were dried over sodium sulfate and evaporated to dryness under reduced pressure. The residue (285 mg) was purified by flash chromatography (SiO$_2$, chloroform/methanol/ammonia 95/5/0.1) to give after trituration in diisopropylether 70 m g of (E,Z)-3-[3-(2-N,N-dimethylaminoethoxyimino)(Z)-propen-1-yl]-5α-androstan-6α,17β-diol-(I-g), as a white podwer mp 111–114° C.

EXAMPLE 7
(E,Z)-3-(2-aminoethoxyimino)-5α-androstan-6,17-dione emioxalate (I-h)

o-Iodoxybenzoic acid (560 mg) was added in one portion to a solution of (E,Z)-3-(2-aminoethoxyimino)-5α-androstan-6α,17β-diol (I-a, 290 mg) and trifluoroacetic acid (60 μL) in dimethylsulfoxide (9 mL). The reaction mixture was stirred overnight, then it was diluted with sodium hydroxide (0.1 N) and extracted with chloroform (3×50 mL). The combined organic layers were dried over sodium sulfate and evaporated to dryness under reduced pressure. The residue was purified by flash chromatography (SiO$_2$, chloroform/methanol/ammonia 90/10/1) and treated with oxalic acid to give 250 mg of (E,Z)-3-(2-aminoethoxyimino)-5α-androstan-6,17-dione emioxalate (I-h), mp 148–151° C.

EXAMPLE 8
(Z)-3-(2-N,N-dimethylaminoethoxyimino)-5α-androstan-6,17-dione (I-i)

o-Iodoxybenzoic acid (300 mg) was added in one portion to a solution of (Z)-3-(2-N,N-dimethylaminoethoxyimino)-5α-androstan-6α,17β-diol (I-c, 140 mg) in dimethylsulfoxide (4 mL). The reaction mixture was stirred overnight, then it was diluted with sodium hydroxide (0.1 N) and extracted with ethyl acetate (3×20 mL). The combined organic layers were dried over sodium sulfate and evaporated to dryness under reduced pressure. The residue (160 mg) was purified by flash chromatography (SiO$_2$, chloroform/methanol/ammonia 90/10/1) to give 100 mg of (Z)-3-(2-N,N-dimethylaminoethoxyimino)-5α-androstan-6,17-dione (I-i), as a light yellow solid, mp 141–145° C.

EXAMPLE 9
(E)-3β-(2-N,N-dimethylaminoethoxyiminomethyl)-5α-androstan-6,17-dione oxalate (I-j)

Using the same reaction conditions described in Ex. 8, and starting from (Z)-3β-(2-N,N-dimethylaminoethoxyiminomethyl)-5α-androstan-6α,17β- diol (I-e, Ex. 4) the title compound (E,Z)-3β-(2-N,N-dimethylaminoethoxyiminomethyl)-5α-androstan-6,17-dione oxalte (I-j) was obtained as a solid mp 162–164° C.

EXAMPLE 10
(E)-3-[3-(2-N,N-dimethylaminoethoxyimino)(E)-propen-1-yl)-5α-androstan-6,17-dione oxalate-(I-k)

Using the same reaction conditions described in Ex. 8, and starting from (E)-3-[3-(2-N,N-dimethylaminoethoxyimino)(E)-propen-1-yl)-5α-androstan-6α,17β-diol (I-f; Ex; 5) the title compound (E,Z)-3-[3-(2-N,N-dimethylaminoethoxyimino)(E)-propen-1-yl)-5α-androstan-6,17-dione oxalate (I-k) was obtained as a solid mp 177–178° C.

EXAMPLE 11
3β-(3-N,N-dimethylaminopropoxy)-5α-androstan-6α,17β-diol (I-l)

Sodium hydride (300 mg, 60% dispersion in oil) was added to a solution of 6α,17β-diethoxymethoxy-5α-androstan-3β-ol (II-f, Prep. 5, 1.8 g) and 3-N,N-dimethylamino-1-chloropropane (1.7 g) in 25 ml of anhydrous tetrahydrofuran, under argon atmosphere at room temperature. The mixture was refluxed for 32 hrs. then it was cooled to room temperature, brine and ethyl acetate were added, the organic layer separated and extracted several times with HCl 1N. The collected aqueous phase was neutralised with potassium hydroxide 4N and extracted with chloroform to give, after workup, a brown-yellowish oil which was dissolved in acetonitrile/water (85/15, 60 mL). p-Toluensulfonic acid was added to pH=0.9 and the reaction mixture stirred for 24 hrs. After usual work-up the residue was purified by flash chromatography (SiO$_2$, chloroform/methanol/ammonia 90/10/1) to give 400 mg of 3β-(3-N,N-dimethylamino propoxy)-5α-androstan-6α,17β-diol (I-l) as a white solid, mp 117–123° C.

EXAMPLE 12
3β-(3-N,N-dimethylaminopropoxy)-5α-androstan-6,17-dione (I-m)

o-Iodoxybenzoic acid (500 mg) was added in one portion to a solution of 3β-(3-N,N-dimethylaminopropoxy)-5α-androstan-6α,17β-diol (I-l, 200 mg) in dimethylsulfoxide (8 mL), and the reaction mixture stirred overnight. It was diluted with sodium hydroxide (0.1 N) and extracted with chloroform (3×30 mL). The combined organic layers were dried over sodium sulfate and evaporated to dryness under reduced pressure. The residue was purified by flash chromatography (SiO$_2$, chloroform/methanol/ammonia 90/10/1) to give 140 mg 3β-(3-N,N-dimethylaminopropoxy)-5α-androstan-6,17-dione (I-m) as a light yellow solid, mp 124–125° C.

EXAMPLE 13
3β-(2-N-pyrrolidinylethoxy)-5α-androstan-6,17-dione (I-n)

Using the same reaction conditions described in Exs. 11 and 12, and starting from 6α,17β-diethoxymethoxy-5α-androstan-3β-ol (II-f, Prep. 5) and N-(2-chloroethyl)-pyrrolidine the title compound 3β-(2-N-pyrrolidinylethoxy)-5α-androstan-6,17-dione (I-n) was obtained 136–140° C.

EXAMPLE 14
3β-(4-N,N-dimethylaminobutoxy)-5α-androstan-6,17-dione (I-o)

Using the same reaction conditions described in Exs. 11 and 12, and starting from 6α,17β-diethoxymethoxy-5α-androstan-3β-ol (II-f, Prep. 5) and 4-N,N-dimethylamino-1-chlorobutane the title compound 3β-(4-N,N-dimethylaminobutoxy)-5α-androstan-6,17-dione (I-o) was obtained as a viscous oil. $^1$H-NMR (300 MHz, CDCl$_3$, ppm from TMS): 3.60–3.40 (4H, m), 3.25 (1H, m), 2.55–1.20 (30H, m) 0.90 (3H, s), 0.78 (3H, s).

EXAMPLE 15
3β-[2-(2-N-pyrrolidinylethoxy)ethoxy]-5α-androstan-6,17-dione oxalate (I-p)

Using the same reaction conditions described in Exs. 11 and 12, and starting from 6α,17β-diethoxymethoxy-5α-androstan-3β-ol (II-f, Prep. 5) and 2-(2-N-pyrrolidinyl)ethoxy-1-chloroethane the title compound 3β-[2-(2-N-pyrrolidinylethoxy)ethoxy]-5α-androstan-6,17-dione was obtained and purified as oxalate salt (I-p) mp 69–73° C.

EXAMPLE 16
3β-[2-(2-N,N-dimethylaminoethoxy)ethoxy]-5α-androstan-6,17-dione (I-q)

Using the same reaction conditions described in Exs. 11 and 12, and starting from 6α,17β-diethoxymethoxy-5α-androstan-3β-ol (II-f, Prep. 5) and 2-(2-N,N-dimethylamino)ethoxy-1-chloroethane the title compound 3β-[2-N,N-dimethylaminoethoxy)ethoxy]-5α-androstan-6,17-dione (I-q) was obtained as an amorphous solid. $^1$H-NMR (300 MHz. CDCl$_3$, ppm from TMS): 3.80–3.50 (8H, m), 3.25 (1H, m), 2.60–1.20 (26H, m) 0.90 (3H, s), 0.78 (3H, s).

EXAMPLE 17
3β-(3-N,N-dimethylaminopropoxy)-5α-androstan-6β,17β-diol (I-r)

Sodium borohydride (70 mg) was added to a solution of 3β-(3-N,N-dimethylaminopropoxy)-5α-androstan-6,17-dione (I-m, Ex. 12, 350 mg) in methanol (10 mL) and the reaction mixture was stirred overnight at room temperature. Glacial acetic acid was added and the reaction mixture is evaporated to dryness under reduced pressure. The residue was purified by flash chromatography (SiO$_2$, chloroform/methanol/ammonia 90/10/1) to give 320 mg 3β-(3-N,N-dimethylaminopropoxy)-5α-androstan-6β,17β-diol, mp 161–166° C.

Preparation 1
3β-tert-Butyldimethylsilyloxy-5α-androstan-6α,17β-diol (II-a)

tert-Butyldimethylsilylchloride (9.72 g) was added, at room temperature, to a solution of prasterone (V, 15 g) in pyridine (60 mL). After 24 hrs, the reaction mixture was poured into iced water (600 mL). Ethyl acetate was added, the two layers were separated, the organic layer washed with sodium bicarbonate (5%), sodium dihydrogenphosphate (5%) and brine, dried over sodium sulfate and evaporated to dryness under reduced pressure. The crude residue, [3β-tert-butyldimethylsilyloxy-androst-5-en-17-one, g 23.9; $^1$H-NMR (300 MHz. CDCl$_3$, ppm from TMS): 5.32 (1H, d), 3.48 (1H, hept), 2.49 (1H, dd), 2.35–0.8 (33H, m), 0.03 (6H, s)] was dissolved in diethyl ether/ethanol (335 mL/250 mL), cooled to 0° C. and treated with sodium borohydride (4 g). The reaction mixture was stirred at room temperature for 1 hr. then quenched with 1N hydrochloric acid to pH=7, diluted with brine (300 mL) and extracted with diethyl ether. The organic layer was separated, dried over sodium sulfate and evaporated to dryness under reduced pressure. The crude residue, [3β-tert-butyldimethylsilyloxy-androst-5-en-17β-ol, g 21; $^1$H-NMR (300 MHz, CDCl$_3$, ppm from TMS): 5.32 (1H, m), 3.62 (1H, m), 3.48 (1H, hept), 2.35–0.8 (34H, m), 0.03 (6H, s)] was dissolved in tetrahydrofurane (850 mL), cooled to 0° C. and treated with boranedimethylsulfide complex (THF, 1M, 155 mL). The reaction mixture was stirred at room temperature for 2 hrs, then it was cooled to 0° C. and quenched with water (300 mL), and sodium perborate tetrahydrate (43 g). The mixture was stirred overnight at room temperature, ammonium chloride (30%, 300 mL) was added, the two layers were separated, the organic one dried over sodium sulfate and evaporated under reduced pressure. The crude residue was purified by flash-chromatography (SiO$_2$; n-hexane/ethyl acetate 75/25) to give to give 18 g of the title compound (II-a) as a foam. $^1$H-NMR (300 MHz, CDCl$_3$, ppm from TMS): 3.68 (1H, t), 3.52 (1H, hept), 3.42 (1H, dd), 2.20–0.6 (35H, m), 0.03 (6H, s).

Preparation 2

3-oxo-5α-androstan-6α,17β-diol (II-b)

A solution of 3β-tert-butyldimethylsilyloxy-5α-androstan-6α,17β-diol (II-a, Prep. 1) (20 g) and acetic anhydride (25 mL) in anhydrous pyridine (50 mL) was stirred at room temperature 24 hrs. The mixture was then poured into ice and water and extracted with ethyl acetate to give after usual workup crude 3β-tert-butyldimethylsilyloxy-6α,17β-diacetoxy-5α-androstane, [23 g, $^1$H-NMR (300 MHz, CDCl$_3$, ppm from TMS): 4.67 (1H, dd), 4.58 (1H, t), 3.50 (1H, hept)], used as such in the next reaction without further purification. This intermediate was deprotected with tetrabutylammonium fluoride (21 g) in THF (350 mL), to give 6α,17β-diacetoxy-5α-androstan-3β-ol [18 g, $^1$H-NMR (300 MHz, CDCl$_3$, ppm from TMS): 4.67 (1H, dd), 4.58 (1H, t), 3.55 (1H, hept)], used as such in the next reaction without further purification. A solution of 6α,17β-diacetoxy-5α-androstan-3β-ol (18 g) and o-iodoxybenzoic acid (27 g) in dimethylsulfoxide (180 mL) was stirred at room temperature overnight, then diluted with water (1.5 L) and diethyl ether (400 mL) and filtered. The two layers were separated, the waters extracted with diethyl ether (3×200 mL), the combined organic layers dried over sodium sulfate and evaporated to dryness under reduced pressure, to give 17 g of 6α,17β-diacetoxy-5α-androstan-3-one. The crude residue was dissolved in methanol (380 mL) and sodium hydroxide (4N, 125 mL), was stirred at room temperature for 1 hr. It was then evaporated to dryness under reduced pressure, the residue dissolved in dichloromethane (600 mL) and water (5000 mL). The two layers were separated and the water extracted with dichloromethane (3×100 mL). The combined organic layers were washed with hydrochloric acid (1N) and water, dried over sodium sulfate and evaporated under reduced pressure to give 15 g of a crude residue, that was purified by flash-chromatography (SiO$_2$; chloroform/methanol 99/1) to give 12 g of 3-oxo-5α-androstan-6α,17β-diol (II-b) as a white solid, mp 195–205° C.

Preparation 3

3-Formyl-5α-androstan-6α,17β-diol (II-c)

Sodium hydride (50% in mineral oil, 640 mg) was carefully washed with n-hexane, under nitrogen atmosphere. Then anhydrous dimethylsulfoxide (160 mL) and trimethylsolfoxonium iodide (2.9 g) were added and the reaction mixture was stirred to complete dissolution. 3-Oxo-5α-androstan-6α,17β-diol (II-b, Prep. 2, 600 mg) was added and the reaction mixture stirred at room temperature for 2 hrs, then poured into ice and water and extracted with ethyl acetate to give, after usual workup, 3-spiro-oxirane-5α-androstan-6α,17β-diol [590 mg,$^1$H-NMR [$^1$H-NMR (300 MHz, CDCl$_3$, ppm from TMS): 3.65 (1H, t), 3.39 (1H, m), 2.70–2.60 (2H, m)]. Freshly distilled borontrifluoride-diethylether complex (300 μL) was added to a solution of crude 3-spiro-oxirane-5α-androstan-6α,17β-diol (590 mg) in anhydrous tetrahydrofurane (25 mL) at −30° C., under nitrogen atmosphere. After 70 minutes, the reaction mixture was poured into disodium hydrogen phosphate (5%), extracted with chloroform (3×50 mL), the combined organic layers were separated and dried over anhydrous sodium sulfate to give, after evaporation to dryness, 530 mg of crude 3-formyl-5α-androstan-6α,17β-diol (II-c) as an amorphous solid (3β-formyl/3β-formyl=⅙ determined by $^1$H-NMR). $^1$H-NMR (300 MHz, CDCl$_3$, ppm from TMS): 9.71 (1H, s), 9.67 (1H, s), 3.75 (1H, m), 3.65 (1H, t), 3.50 (1H, m), 2.40–0.6 (25H, m).

Preparation 4

(E)-3-Formylmethylen-5α-androstan-6α,17β-diol (II-d) and (Z)-3-formylmethylen-5α-androstan-6α,17β-diol (II-e)

Trimethyl phosphonoacetate (1.9 mL) was added to a mixture of sodium hydride (50%, 500 mg) in anhydrous tetrahydrofurane (25 mL), and the mixture was stirred at room temperature under nitrogen atmosphere for 15 min, then 3-oxo-5α-androstan-6α,17β-diol (II-b, Prep. 2.0 g) dissolved in anhydrous tetrahydrofurane (5 mL) was added. After 1 hr the reaction was quenched with sodium dihydrogen phosphate (5%). The mixture was extracted several times with ethyl acetate, the combined organic layers were dried over anhydrous sodium sulfate and evaporated to dryness under reduced pressure. The crude residue was purified by chromatography (SiO$_2$; n-hexane/ethyl acetate 50/50) to give 780 mg of (E)-3-methoxycarbonylmethylen-5α-androstan-6α,17β-diol and 1.04 g of (Z)-3-methoxycarbonylmethylen-5α-androstan-6α,17β-diol as amorphous solids. (E)-3-methoxycarbonylmethylen-5α-androstan-6α,17β-diol $^1$H-NMR (300 MHz, CDCl$_3$, ppm from TMS): 5.65 (1H, bs), 3.75 (1H, m), 3.65 (3H, s), 3.52 (1H, t), 3.48 (1H, ddd), 2.55 (1H, m), 2.20–0.6 (24H, m). (Z)-3-methoxycarbonylmethylen-5α-androstan-6α,17β-diol $^1$H-NMR (300 MHz, CDCl$_3$, ppm from TMS): 5.62 (1H, bs), 4.10 (1H, m), 3.65 (3H, s), 3.52 (1H, t), 3.48 (1H, ddd), 2.40–0.6 (25H, m). Diisobutylaluminum hydride (1M in hexane, 10 mL) was added at −78° C. to a solution of (E)-3-methoxycarbonylmethylen-5α-androstan-6α,17β-diol (700 mg) in anhydrous tetrahydrofurane (25 mL) under nitrogen atmosphere. The mixture was stirred overnight, then it was quenched (−78° C.) with sulfuric acid (0.1N, to pH=3–4) and extracted with ethyl acetate. The organic layers were dried over anhydrous sodium sulfate and evaporated to dryness under reduced pressure. The residue was purified by flash chromatography (SiO$_2$, n-hexane/chloroform/acetone 10/45/45) to give 640 mg of (E)-3-(2-hydroxyethylen)-5α-androstan-6α,17β-diol. $^1$H-NMR (300 MHz, CDCl$_3$, ppm from TMS): 5.35 (1H, m), 4.10 (2H, m), 3.52 (1H, t), 3.48 (1H, m), 2.55 (1H, m), 2.20–0.6 (25H, m). A mixture of (E)-3-(2-hydroxyethylen)-5α-androstan-6α, 17β-diol (630 mg) and manganese dioxide (3 g) in dioxane (60 mL) was stirred at room temperature for 40 hrs, then it was filtered on a celite pad. The organic solution was dried over sodium sulfate and evaporated to dryness under reduced pressure. to give 530 mg of (E)-3-formylmethylen-5α-androstan-6α,17β-diol (II-d) $^1$H-NMR (300 MHz, CDCl$_3$, ppm from TMS): 10.03 (1H, d), 5.90 (1H, m) 3.65 (1H, t), 3.48 (1H, m), 3.28 (1H, m), 2.55 (1H, m), 2.20–0.6 (24H, m). Similarly, starting from (Z)-3-methoxycarbonylmethylen-5α-androstan-6α,17β-diol and using the experimental conditions above described it was possible to prepare (Z)-3-formylmethylen-5α-androstan-6α, 17β-diol (II-e) $^1$H-NMR (300 MHz, CDCl$_3$, ppm from TMS): 10.08 (1H, d), 5.82 (1H, m) 3.65 (1H, t), 3.52 (1H, m), 2.50–0.6 (26H, m).

Preparation 5
6α,17β-Diethoxymethoxy-5α-androstan-3β-ol (I-f)

A solution of 3β-tert-butyldimethylsilyloxy-5α-androstan-6α,17β-diol (II-a, Prep. 1, 10 g), chloromethyl ethyl ether (16 mL) and di-iso-propylethylamine (120 mL) in dry dichloromethane (500 mL) was stirred overnight at 0° C. Citric acid (10% water solution, 1.5 L) was added, the organic layer separated, washed with water and dried over anhydrous sodium sulfate. The solvent was removed in vacuo. The residue was purified by chromatography (hexane/ethyl acetate 85/15) to give 10.8 g of 3β-tert-butyldimethylsilyloxy-6α,17β-di-ethoxymethoxy-5α-androstane. $^1$H-NMR (300 MHz, CDCl$_3$, ppm from TMS): 4.60 (4H, m), 3.70–3.40 (7H, m), 2.20–0.6 (41H, m), 0.03 (6H, s).

This intermediate was deprotected with tetrabutylammonium fluoride (12 g) in THF (100 ml), to give 7.7 g of 6α,17β-di-ethoxymethoxy-5α-androstan-3β-ol as an amorphous solid. $^1$H-NMR (300 MHz, CDCl$_3$, ppm from TMS): 4.62 (4H, m), 3.70–3.40 (7H, m), 2.20–0.6 (32H, m).

We claim:

1. 6-hydroxy and 6-oxo-androstane derivatives of the general formula (I)

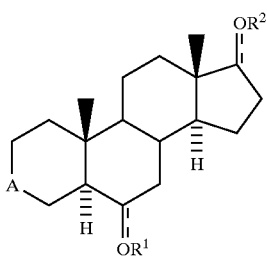

wherein:
the symbol A represents CH—OR, C=N—OR, CH—CH=N—OR and C=CH—CH=N—OR,
where:
R represents a C2–C6 alkyl group substituted by NR$^3$R$^4$, NHC(NH)NHR$^5$, C(NH)NR$^6$R$^7$ or —O—(C2–C4alkyl)—NR$^3$R$^4$ groups,
wherein R$^3$ and R$^4$, which may be the same or different, are H, C1–C6 lower alkyl group, benzyl or phenyl or R$^3$ and R$^4$, taken together with the nitrogen atom, form an unsubstituted or substituted saturated or unsaturated mono-heterocyclic 5-or 6-membered ring optionally containing another heteroatom chosen from oxygen, sulphur or nitrogen,
R$^5$, R$^6$ and R$^7$, which are the same or different, may be H or C1–C4 lower alkyl;
the symbol ———. in position 6 and in position 17 represents independently a single or a double bond;
when the symbol ———. represents a single bond
R$^1$ represents H, C1–C4 lower alkyl and C1–C6 acyl groups;
R$^2$ represents H, methyl, C2–C6 alkyl group unsubstituted or substituted by NR$^3$R$^4$, C2–C6 acyl groups, benzoyl, benzoyl substituted by one or more hydroxy, methoxy, amino, chloro, fluoro, methylmercapto groups;
when the symbol ———. represent a double bond, it means a keto group and no R$^1$or R$^2$ is present.

2. Stereoisomers, Z and E isomers, syn and anti isomers, optical isomers, pharmaceutically acceptable salts and mixtures thereof of the compounds of formula (I).

3. A compound of formula (I) selected from:
3β-(4-N-ethylaminobutoxy)-5α-androstan-6,17-dione
3β-(2-N,N-dimethylaminoethoxy)-5α-androstan-6,17-dione
3α-(3-N,N-dimethylaminopropoxy)-5α-androstan-6,17-dione
3β-(3-N,N-dimethylaminopropoxy)-5α-androstan-6,17-dione
3β-(4-N,N-dimethylaminobutoxy)-5α-androstan-6,17-dione
3β-(2-N-pyrrolidinylethoxy)-5α-androstan-6,17-dione
3β-[2-(2-N,N-dimethylaminoethoxy)ethoxy]-5α-androstan-6,17-dione
3β-[2-(2-N-pyrrolidinylethoxy)ethoxy]-5α-androstan-6, 17-dione
3β-(2-N-imidazolylethoxy)-5α-androstan-6,17-dione
3β-(3-N-imidazolylpropoxy)-5α-androstan-6,17-dione
3β-(2-N-piperidinoethoxy)-5α-androstan-6,17-dione
3β-[2-(4-methylpiperazin-1-yl)ethoxy)]-5α-androstan-6, 17-dione
3β-(2-aminoethoxy)-5α-androstan-6α,17β-diol
3β-(3-aminopropoxy)-5α-androstan-6α,17β-diol
3β-(3-N-methylaminopropoxy)-5α-androstan-6α,17β-diol
3β-(2-N,N-dimethylaminoethoxy)-5α-androstan-6α,17β-diol
3α-(3-N,N-dimethylaminopropoxy)-5α-androstan-6α,17β-diol
3β-(3-N,N-dimethylaminopropoxy)-5α-androstan-6α,17β-diol
3β-(4-N,N-dimethylaminobutoxy)-5α-androstan-6α,17β-diol
3β-(2-N-pyrrolidinylethoxy)-5α-androstan-6α,17β-diol
3β-[2-(2-N,N-dimethylaminoethoxy)ethoxy]-5α-androstan-6α,70β-diol
3β-[2-(2-N-pyrrolidinylethoxy)ethoxy]-5α-androstan-6α,17β-diol
3β-(2-aminoethoxy)-5α-androstan-6β,17β-diol
3β-(3-N,N-dimethylaminopropoxy)-5α-androstan-6β,17β-diol
3β-(2-guanidinoethoxy)-5α-androstan-6β,17β-diol
3β-(3-guanidinopropoxy)-5α-androstan-6β,17β-diol
3β-(2-guanidinoethoxy)-5α-androstan-6β,17β-diol
3β-[2-(2-N,N-dimethylaminoethoxy)ethoxy]-5α-androstan-6β,17β-diol
3β-(2-N,N-dimethylaminoethoxy)-5α-androstan-17β-acetate-6α-ol
3β-(3-N,N-dimethylaminopropoxy)-5α-androstan-17β-acetate-6α-ol
3β-(3-N,N-dimethylaminopropoxy)-5α-androstan-17β-benzoate-6α-ol
3β-(3-N,N-dimethylaminopropoxy)-5α-androstan-17β-(2-N,N-dimethylaminoethoxy)-6α-ol
3β-(2-aminoethoxy)-5α-androstan-6α-hydroxy-17-one
3β-(2-N-ethylaminoethoxy)-5α-androstan-6α-hydroxy-17-one
3β-(3-N,N-dimethylaminopropoxy)-5α-androstan-6α-hydroxy-17-one
3β-(2-N,N-dimethylaminoethoxy)-5α-androstan-17β-hydroxy-6-one (E,Z)-3-(2-aminoethoxyimino)-5α-androstan-6,17-dione
(E)-3-(2-aminoethoxyimino)-5α-androstan-6,17-dione
(Z)-3-(2-aminoethoxyimino)-5α-androstan-6,17-dione
(E)-3-(2-N,N-dimethylaminoethoxyimino)-5α-androstan-6,17-dione
(Z)-3-(2-N,N-dimethylaminoethoxyimino)-5α-androstan-6,17-dione
(E)-3β-(2-aminoethoxyiminomethyl)-5α-androstan-6,17-dione
(Z)-3β-(2-aminoethoxyiminomethyl)-5α-androstan-6,17-dione
(E)-3β-(2-N,N-dimethylaminoethoxyiminomethyl)-5α-androstan-6,17-dione
(Z)-3β-(2-N,N-dimethylaminoethoxyiminomethyl)-5α-androstan-6,17-dione
(E)-3-[3-(2-N,N-dimethylaminoethoxyimino)(E)-propen-1-yl]-5α-androstan-6,17-dione
(Z)-3-[3-(2-N,N-dimethylaminoethoxyimino)(E)-propen-1-yl]-5α-androstan-6,17-dione
(E)-3-[3-(2-N,N-dimethylaminoethoxyimino)(Z)-propen-1-yl]-5α-androstan-6,17-dione
(Z)-3-[3-(2-N,N-dimethylaminoethoxyimino)(Z)-propen-1-yl]-5α-androstan-6,17-dione
(E,Z)-3-(2-aminoethoxyimino)-5α-androstan-6α,17β-diol
(E)-3-(2-N,N-dimethylaminoethoxyimino)-5α-androstan-6α,17β-diol
(Z)-3-(2-N,N-dimethylaminoethoxyimino)-5α-androstan-6α,17β-diol
(E)-3β-(2-aminoethoxyiminomethyl)-5α-androstan-6α,17β-diol
(Z)-3β-(2-aminoethoxyiminomethyl)-5α-androstan-6α,17β-diol
(E)-3β-(2-N,N-dimethylaminoethoxyiminomethyl)-5α-androstan-6α,17β-diol
(Z)-3β-(2-N,N-dimethylaminoethoxyiminomethyl)-5α-androstan-6α,17β-diol
(E)-3-[3-(2-N,N-dimethylaminoethoxyimino)(E)-propen-1-yl]-5α-androstan-6α,17β-diol
(Z)-3-(3-(2-N,N-dimethylaminoethoxyimino)(E)-propen-1-yl]-5α-androstan-6α,17-diol
(E,Z)-3-[3-(2-N,N-dimethylaminoethoxyimino)(Z)-propen-1-yl]-5α-androstan-6α,17β-diol
(E)-3-[3-(2-N,N-dimethylaminoethoxyimino)(Z)-propen-1-yl]-5α-androstan-6α,17β-diol
(Z)-3-[3-(2-N,N-dimethylaminoethoxyimino)(Z)-propen-1-yl]-5α-androstan-6α,17β-diol.

4. A pharmaceutical composition comprising a compound of claim 1, 2 or 3 and a pharmacologically acceptable excipient therefor.

5. The compound of claim 1, which is (E,Z)-3-(2-aminoethoxyimino)-5α-androstan-6,17-dione hemioxalate.

6. A method for the treatment of a patient having a cardiovascular disorder, comprising: administering to said patient an effective amount of a compound of claim 1, or a pharmaceutically acceptable salt thereof.

7. The method of claim 6 wherein said cardiovascular disorder is hypertension.

8. The method of claim 6 wherein said cardiovascular disorder is cardiac failure.

* * * * *